(12) United States Patent
DeMan et al.

(10) Patent No.: US 7,760,848 B2
(45) Date of Patent: Jul. 20, 2010

(54) METHOD AND SYSTEM FOR GENERATING A MULTI-SPECTRAL IMAGE OF AN OBJECT

(75) Inventors: Bruno Kristiaan Bernard DeMan, Clifton Park, NY (US); Samit Kumar Basu, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 687 days.

(21) Appl. No.: 11/530,288

(22) Filed: Sep. 8, 2006

(65) Prior Publication Data

US 2008/0063135 A1 Mar. 13, 2008

(51) Int. Cl.
*A61B 6/03* (2006.01)

(52) U.S. Cl. .............................. 378/4; 378/901; 382/131

(58) Field of Classification Search ...................... 378/4, 378/901; 382/131
See application file for complete search history.

(56) References Cited

U.S. PATENT DOCUMENTS

| | | | |
|---|---|---|---|
| 6,324,240 B1 * | 11/2001 | Yan et al. | 378/4 |
| 6,947,584 B1 * | 9/2005 | Avila et al. | 382/131 |
| 2003/0156684 A1 * | 8/2003 | Fessler | 378/210 |
| 2004/0264627 A1 * | 12/2004 | Besson | 378/5 |
| 2005/0105693 A1 * | 5/2005 | Zhao et al. | 378/210 |

OTHER PUBLICATIONS

De Man et al., An Iterative Maximum-Likelihood Polychromatic Algorithm for CT, 2001, IEEE Transactions on Medical Imaging, vol. 20, No. 10, pp. 999-1008.*

Menvielle et al., Reduction in Beam-Hardening Artifacts in X-Ray CT, Sep. 4, 2005, Proceedings of the IEEE Engineering in Medicine and Biology 27th Annual Conference, pp. 1865-1868.*

La Riviere et al., Monotonic Penalized-Likelihood Image Reconstruction for Fluorescence Computed Tomography, Oct. 29, 2005, IEEE Nuclear Science Symposium, M07-95, vol. 4, pp. 1991-1995.*

Stonestrom et al., A Framework for Spectral Artifact Corrections in X-ray CT, 1981, IEEE Transactions on Biomedical Engineering, vol. BME-28, No. 2, pp. 128-141.*

Benac, Alternating Minimization Algorithms for X-ray Computed Tomography: Multigrid Acceleration and Dual Energy Applications, May 2005, Doctoral Dissertation, Washington University Sever Institute of Technology Department of Electrical Engineering, 113 pages.*

Elbakri et al., Statistical Image Reconstruction for Polyenergetic X-ray Computed Tomography, 2002, IEEE Transactions on Medical Imaging, vol. No. 2, pp. 89-99.*

(Continued)

*Primary Examiner*—Edward J Glick
*Assistant Examiner*—John M Corbett
(74) *Attorney, Agent, or Firm*—Jason K. Klindtworth (57) ABSTRACT

A method for generating a multi-spectral image of an object is provided. The method comprises acquiring measurement data at a plurality of X-ray energy levels and defining a plurality of image voxels in one or more regions comprising the object. The method then comprises obtaining prior information associated with a plurality of image voxels comprising the object. The prior information is defined by a joint probability density function (PDF) between a plurality of basis components. The method further comprises reconstructing the measurement data to generate a multi-spectral reconstructed image of the object based on the prior information.

21 Claims, 6 Drawing Sheets

OTHER PUBLICATIONS

Zhang et al., Experimental evaluation for joint estimation approach, 1996, IEEE Nuclear Science Symposium on Medical Imaging, vol. 3, pp. 1623-1627.*

La Riviere et al., Penalized-likelihood image reconstruction for x-ray fluorescence computed tomography with unknown fluorescence attenuation maps, 2004, SPIE, vol. 5535, pp. 243-252.*

Schroer, Reconstructing x-ray fluorescence microtomograms, Applied Physics Letters, 2001, vol. 79, No. 12, pp. 1912-1914.*

La Riviere et al., Penalized-likelihood sinogram decomposition for dual-energy computed tomography, 2008, IEEE Nuclear Science Symposium, pp. 5166-5169.*

Homem, The linear attenuation coefficients as features of multiple energy CT image classification, 2000, Nuclear Instrumentation Methods in Physics Research A, vol. 452, pp. 351-360.*

Bowsher et al., Bayesian Reconstruction and Use of Anatomical A Priori Information for Emission Tomography, 1996, IEEE Transactions on Medical Imaging, vol. 15, No. 5, pp. 673-686.*

* cited by examiner

METHOD AND SYSTEM FOR GENERATING A MULTI-SPECTRAL IMAGE OF AN OBJECT

BACKGROUND

The invention relates generally to the field of image reconstruction. In particular, the invention relates to a technique for defining prior information for multi-spectral images. More particularly, the invention relates to a technique for generating a multi-spectral image based on the prior information.

An imaging system typically operates by projecting X-ray beams from an X-ray source through an attenuating object, such as a patient. The X-ray beams may be collimated between the source and the object into a fan or cone shape, depending on the configuration of the detector optimal patient exposure, or other factors. The attenuated beams are then detected by a set of detector elements. The detector elements produce signals based on the intensity of the X-ray beams. The measured data are then processed to represent the line integrals of the attenuation of the object along the ray paths. The processed data are typically called projections. By using reconstruction techniques, such as filtered backprojection, cross-sectional images are formulated from the projections. Adjacent cross-sectional images may be displayed together to render a volume representing the imaged region of the object or patient.

As will be appreciated by those skilled in the art, the linear attenuation coefficient of a material is a function of two separate events that may occur when an X-ray beam passes through a material. The first event is known as Compton scatter and denotes the tendency of an X-ray photon passing through the material to be scattered or diverted from the original beam path, with a resultant change in energy. The second event is known as photoelectric absorption and denotes the tendency of an X-ray photon passing through the material to be absorbed by the material.

As one might expect, different materials differ in their scatter and absorption properties, resulting in different attenuation coefficients for different materials. In particular, the probability of Compton scattering depends in part on the electron density of the imaged material and the probability of photoelectric absorption depends in part on the atomic number of the imaged material, i.e., the greater the atomic number, the greater the likelihood of absorption. Furthermore, both the Compton scattering effect and photoelectric absorption depend in part on the energy of the X-ray beam. As a result, materials can be distinguished from one another based upon the relative importance of the photoelectric absorption and Compton scattering effects in X-ray attenuation by the material. In particular, measurement of the attenuation produced by a material at two or more X-ray energy levels or using two or more energy spectra, i.e., multi-energy or multi-spectral CT, may allow for respective Compton scattering and photoelectric absorption contributions to be quantified for a material.

Since the decomposition of the attenuation into Compton scattering and photo-electric absorption contributions is not a well defined process, it would be desirable to model the spectral dependence of an image based on prior knowledge about the contribution of Compton scattering and photoelectric absorption in a material. In addition, it would be desirable to use this prior knowledge to generate a multi-spectral image with improved image quality.

BRIEF DESCRIPTION

In one embodiment, a method for generating a multi-spectral image of an object is provided. The method comprises acquiring measurement data at a plurality of X-ray energy levels and defining a plurality of image voxels in one or more regions comprising the object. The method then comprises obtaining prior information associated with the plurality of image voxels comprising the object. The prior information is defined by a joint probability density function (PDF) between a plurality of basis components. The method further comprises reconstructing the measurement data to generate a multi-spectral reconstructed image of the object based on the prior information.

In another embodiment, an image analysis system is provided. The image analysis system comprises an X-ray source configured to emit a stream of radiation and a detector configured to detect the stream of radiation to generate one or more signals responsive to the stream of radiation. The detector comprises a plurality of detector elements. The image analysis system further comprises a system controller and a computer. The system controller is configured to control the X-ray source and to acquire measurement data at a plurality of X-ray energy levels from one or more of the detector elements via a data acquisition system. The computer is configured to define a plurality of image voxels in one or more regions comprising the object and obtain prior information associated with the plurality of image voxels comprising the object. The prior information is defined by a joint probability density function (PDF) between a plurality of basis components. The computer is further configured to reconstruct the measurement data to generate a multi-spectral reconstructed image of the object based on the prior information.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
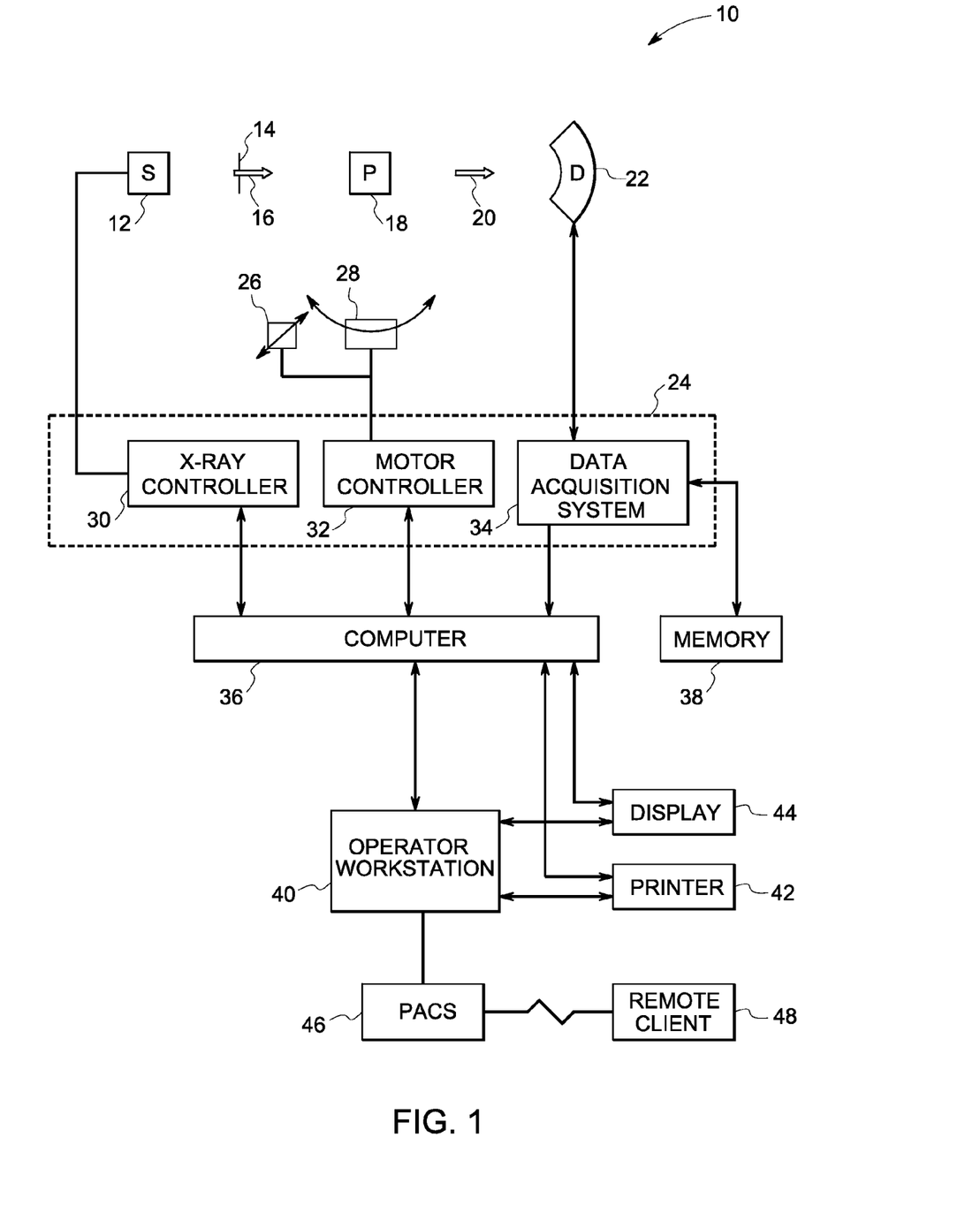
FIG. 1 is an illustration of an image analysis system for acquiring and processing image data in accordance with one embodiment of the invention.

FIG. 1 illustrates diagrammatically an image analysis system 10 for acquiring and processing image data in accordance with one embodiment of the invention. In the illustrated embodiment, system 10 is a multi-energy computed tomography (ME-CT) system designed to acquire image data at two or more X-ray energy levels or spectra and to process the image data for display and analysis in accordance with the present technique. The imaging system 10 may be designed to acquire image data at a single X-ray source spectrum using a detector with energy resolution, which allows the energy level of each detected photon or the average energy level of a subset of the detected photons to be assessed. In the embodiment illustrated in FIG. 1, imaging system 10 includes a source of X-ray radiation 12 positioned adjacent to a collimator 14. In this exemplary embodiment, the source 12 of X-ray radiation is typically an X-ray tube.

Collimator 14 permits a stream of radiation 16 to pass into a region in which a subject, such as a human patient 18 is positioned. A portion of the radiation 20 passes through or around the subject and impacts a detector array, represented generally at reference numeral 22. Detector elements of the array produce electrical signals that represent the intensity of the incident X-ray beam. These signals are acquired and processed to reconstruct an image of the features within the subject.

A system controller 24 may control the source 12. The system controller 24 typically furnishes both power, and control signals for CT examination sequences. Moreover, the detector 22 is coupled to the system controller 24, which controls the acquisition of the signals generated in the detector 22. The system controller 24 may also execute various signal processing and filtration functions, such as for initial adjustment of dynamic ranges, interleaving of digital image data, and so forth. In general, system controller 24 commands operation of the imaging system to execute examination protocols and to process acquired data. In the present context, system controller 24 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 1, system controller 24 is coupled to a linear positioning subsystem 26 and a rotational subsystem 28. The rotational subsystem 28 enables the X-ray source 12, collimator 14 and the detector 22 to be rotated one or multiple turns around the patient 18. It should be noted that the rotational subsystem 28 might include a gantry. Thus, the system controller 24 may be utilized to operate the gantry. The linear positioning subsystem 26 enables the patient 18, or more specifically a patient table, to be displaced linearly. Thus, the patient table may be linearly moved within the gantry to generate images of particular areas of the patient 18.

Additionally, as will be appreciated by those skilled in the art, the source of radiation may be controlled by an X-ray controller 30 disposed within the system controller 24. Particularly, the X-ray controller 30 is configured to provide power and timing signals to the X-ray source 12 and may determine what X-ray energy level or spectrum the source 12 emits. A motor controller 32 may be utilized to control the movement of the rotational subsystem 28 and the linear positioning subsystem 26.

Further, the system controller 24 is also illustrated comprising a data acquisition system 34. In this exemplary embodiment, the detector 22 is coupled to the system controller 24, and more particularly to the data acquisition system 34. The data acquisition system 34 receives data collected by readout electronics of the detector 22. The data acquisition system 34 typically receives sampled analog signals from the detector 22 and converts the data to digital signals for subsequent processing by a computer 36.

The computer 36 is typically coupled to the system controller 24. The measurement data collected by the data acquisition system 34 may be transmitted to the computer 36 for subsequent processing and reconstruction. The computer 36 may comprise or communicate with a memory 38 that can store data processed by the computer 36 or data to be processed by the computer 36. It should be understood that any type of computer accessible memory device capable of storing the desired amount of data and/or code may be utilized by such an exemplary system 10. Moreover, the memory 38 may comprise one or more memory devices, such as magnetic or optical devices, of similar or different types, which may be local and/or remote to the system 10. The memory 38 may store data, processing parameters, and/or computer programs comprising one or more routines for performing the processes described herein.

In a particular embodiment, and as will be described in greater detail below, the computer 36 is configured to define prior information associated with a plurality of image voxels comprising the object. The prior information is defined by a joint probability density function (PDF) between a plurality of basis components of the linear attenuation coefficients in the object. The computer 36 is further configured to reconstruct the measurement data to generate a multi-spectral reconstructed image of the object based on the prior information. The measurement data comprises at least one of density line integral measurements, photo-electric line integral measurements and Compton line integral measurements.

The computer 36 may also be adapted to control features enabled by the system controller 24, i.e., scanning operations and data acquisition. Furthermore, the computer 36 may be configured to receive commands and scanning parameters from an operator via an operator workstation 40 typically equipped with a keyboard and other input devices (not shown). An operator may thereby control the system 10 via the input devices. Thus, the operator may observe the reconstructed image and other data relevant to the system from computer 36, initiate imaging, and so forth.

An operator may control the system 10 via the input devices. Thus, the operator may observe the reconstructed image and other data relevant to the system from computer 36, initiate imaging, and so forth. Similarly, a display 42 coupled to the operator workstation 40 may allow an operator to observe the reconstructed image and to control imaging. Additionally, a reconstructed image may also be printed by a printer 44 which may be coupled to the operator workstation 40. The display 42 and printer 44 may also be connected to the computer 36, either directly or via the operator workstation 40. Further, the operator workstation 40 may also be coupled to a picture archiving and communications system (PACS) 46. It should be noted that PACS 46 might be coupled to a remote client 48, radiology department information system (RIS), hospital information system (HIS) or to an internal or external network, so that others at different locations may gain access to the image and to the image data.

It should be further noted that the computer 36 and operator workstation 40 may be coupled to other output devices, which may include standard, or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Embodiments of the present invention disclose a technique for defining prior information for images acquired at two or more X-ray energy levels or spectra. As used herein, "prior information" refers to composition and density information of one or more materials present in an imaged object. As used herein, "composition" refers to the amount of Compton scattering and photoelectric absorption of a material in an imaged object and "density" refers to the average attenuation of a voxel in an imaged object. Alternatively, "composition" may refer to the amount of any other basis components, such as, the attenuation of water and the attenuation of bone that make up the total attenuation of a given material or a given image voxel. In addition, embodiments of the present invention disclose a technique for generating a multi-spectral image with reduced noise and better material decompositions, based on the prior information. As will be described in greater detail below, the noise reduction is achieved through selective smoothing of the image and material decompositions are achieved through the incorporation of known nominal material properties into the attenuation coefficients of each image voxel.

As will be appreciated by those skilled in the art, an image voxel may be generally characterized by a certain photoelectric absorption density/weight and a Compton scatter density/weight. Since, X-ray attenuation is mainly due to photo-electric absorption and Compton scatter, the linear attenuation in a voxel may be characterized by two parameters $\phi$ and $\theta$, wherein $\phi$ represents the amount of photo-electric absorption in a given tissue or voxel and $\theta$ represents the Compton scatter in a given tissue or voxel.

Given that the energy dependences of the effects due to photo-electric absorption ($\Phi(E)$) and Compton scatter ($\Theta(E)$) are known and independent of material, the linear attenuation of a voxel may be represented as shown in equation (1) below.

$$\mu(E) = \phi \cdot \Phi(E) + \theta \cdot \Theta(E) \quad (1)$$

Since the attenuation of every material may be represented as a linear combination of the two basis functions, $\Phi(E)$ and $\Theta(E)$, any two materials whose $\phi$ and $\theta$ are linearly independent may be chosen to define a new set of basis functions. Typical examples of material compositions may include, but are not limited to, water and bone, or bone and iodine. For example, a de-composition of water and bone may be represented by equation (2), as shown below.

$$\mu(E) = w \cdot W(E) + b \cdot B(E) \quad (2)$$

where w represents the amount of water-equivalent attenuation W(E) and b represents the amount of bone-equivalent attenuation B(E). Equation (2) may be transformed into equation (1) (or vice versa) by substituting:

$$W(E) = c1 \cdot \Phi(E) + c2 \cdot \Theta(E) \quad (3)$$

$$B(E) = c3 \cdot \Phi(E) + c4 \cdot \Theta(E) \quad (4)$$

where c1, c2, c3, and c4 are empirically defined coefficients, representing the contributions of Compton scatter and photo-electric absorption in the attenuation of water and bone respectively. Alternately, ideal materials may be used: e.g., one theoretical material that has no photoelectric absorption and only Compton interactions, and a second theoretical material that has no Compton interactions and only photoelectric absorption. In other words, any physical material can then be represented as a linear combination of these two ideal materials.

Figure 2:
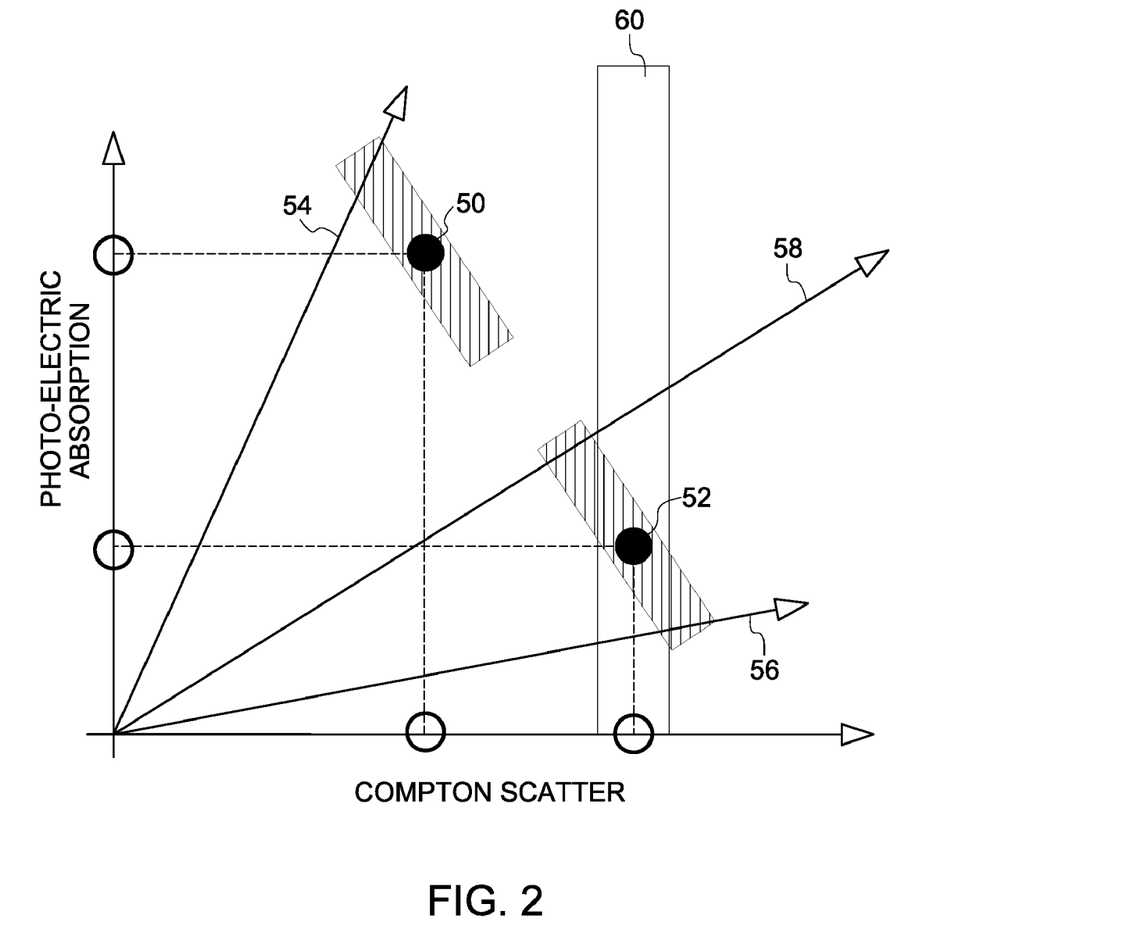
FIG. 2 is a graph illustrating composition and density information in a two-dimensional (2D) space for an image voxel of an imaged object in accordance with one embodiment of the invention.

FIG. 2 is a graph illustrating composition and density information in a two-dimensional (2D) space for an image voxel of an imaged object in accordance with one embodiment of the invention. In a particular embodiment, FIG. 2 is an illustration of prior information in terms of the Compton Scatter distribution of the object or voxel to be re-constructed. As will be appreciated by those skilled in the art, materials may be distinguished from one another based upon the relative importance of the photoelectric absorption and Compton scattering effects in X-ray attenuation by the material. Accordingly, an image voxel may be characterized in a realistic two-dimensional (2D) $\phi$-$\theta$ space instead of mapping it to a one-dimensional effective attenuation ($\mu_{eff}$) space. In other words, the location of an image voxel in a 2D space of an imaged object that is known to correspond to a particular physical material (such as, for example, bone or water) may be characterized by a certain amount of Compton scatter and a certain amount of photo-electric absorption. Referring to FIG. 2 now, reference numerals 50 and 52 correspond to two image voxels in a 2D space of an imaged object comprising different material compositions, such as for example, bone 54 and water 56. Reference numeral 58 represents the effective attenuation axis. Region 60 corresponds to a particular location in the 2D space of an imaged object that is characterized by a certain amount of Compton scatter. As may be appreciated by those skilled in the art, FIG. 2 is an illustration of the Compton Scatter distribution of the object or voxel to be re-constructed.

Figure 3:
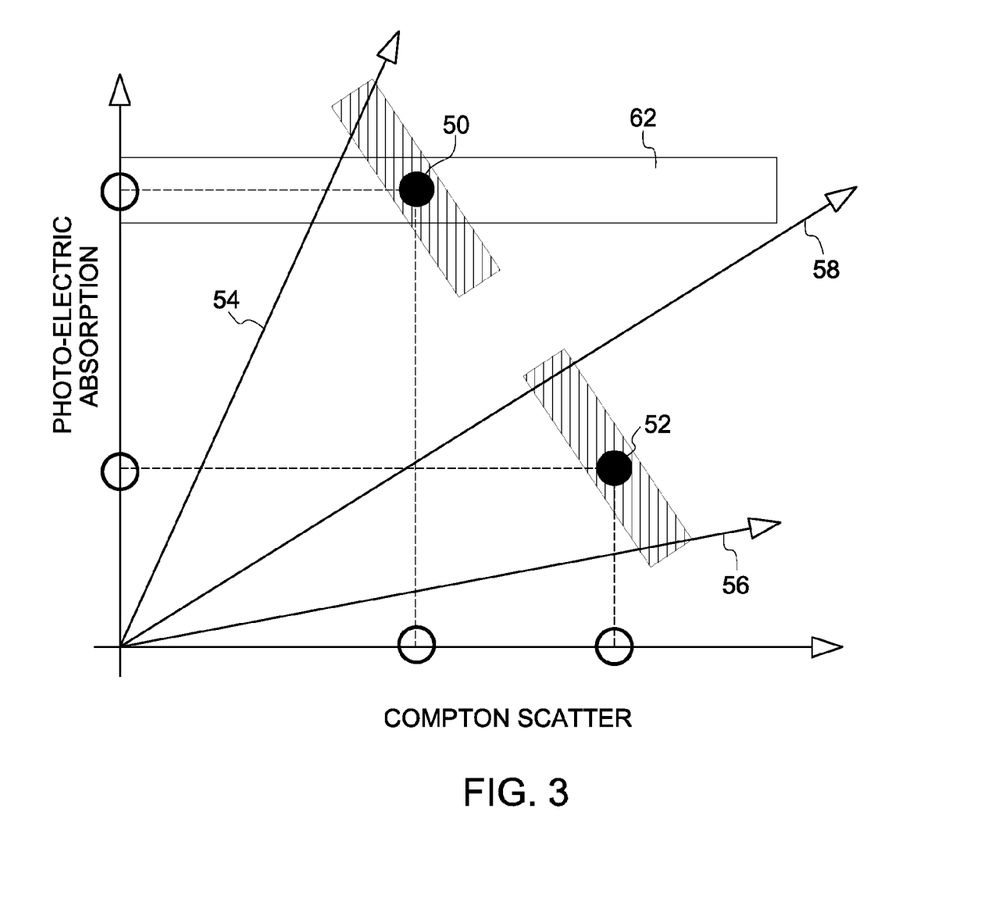
FIG. 3 is a graph illustrating composition and density information in a two-dimensional (2D) space for an image voxel of an imaged object in accordance with another embodiment of the invention.

FIG. 3 is a graph illustrating composition and density information in a two-dimensional (2D) space for an image voxel of an imaged object in accordance with another embodiment of the invention. In a particular embodiment, FIG. 3 is an illustration of prior information in terms of the photo-electric absorption of the object or voxel to be re-constructed. As mentioned above, the location of an image voxel of an imaged object in a 2D space that is known to correspond to a particular physical material (such as, for example, bone or water) may be characterized by a certain amount of Compton scatter and a certain amount of photo-electric absorption. In the particular example shown in FIG. 3, reference numerals 50 and 52 correspond to two image voxels of an imaged object in a 2D space comprising different material compositions, such as for example, bone 54 and water 56. Region 62 corresponds to a particular location in the 2D space of an imaged object that is characterized by a certain amount of photo-electric absorption.

Figure 4:
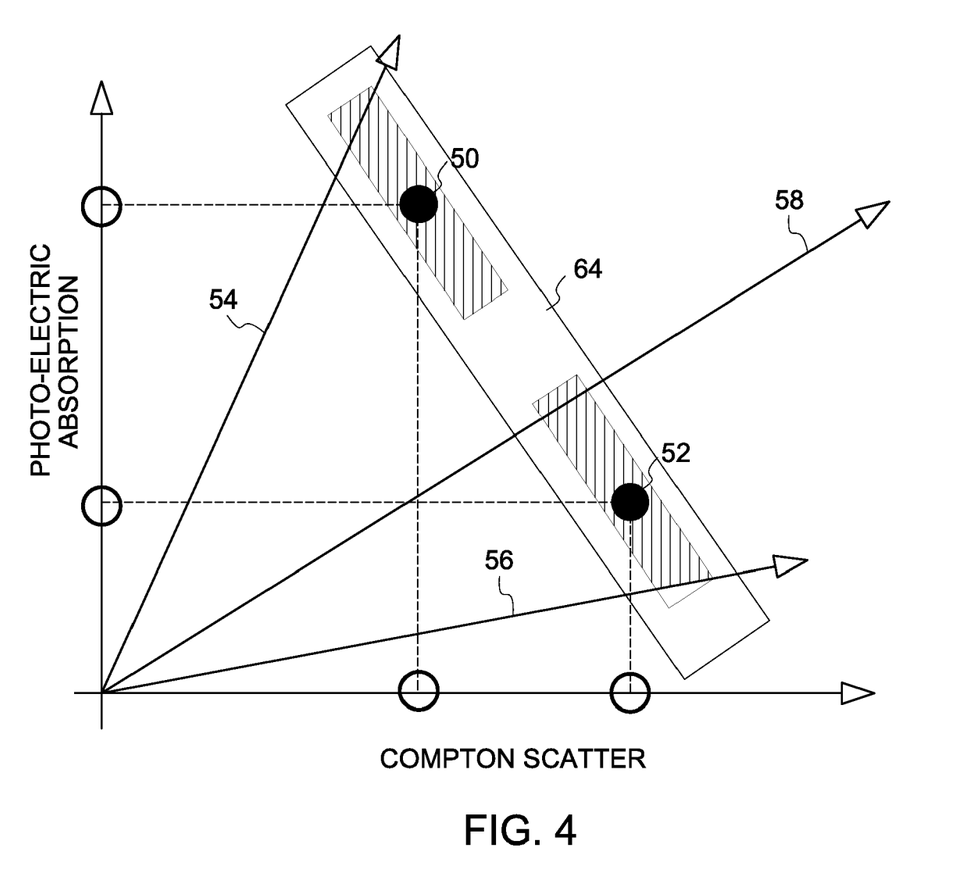
FIG. 4 is a graph illustrating composition and density information in a two-dimensional (2D) space for an image voxel of an imaged object in accordance with yet another embodiment of the invention.

FIG. 4 is a graph illustrating composition and density information in a two-dimensional (2D) space for an image voxel of an imaged object in accordance with yet another embodiment of the invention. In a particular embodiment, FIG. 4 is an illustration of prior information in terms of the effective attenuation of the object or voxel to be re-constructed. Reference numerals 50 and 52 correspond to two image voxels of an imaged object in a 2D space, comprising different material compositions, such as for example, bone 54 and water 56. Reference numeral 58 represents the effective attenuation axis. Region 64 corresponds to a particular location in the 2D space of an imaged object denoting the effective attenuation of a material. As may be observed from the graph of FIG. 4, the average effective attenuation of an image voxel is constant along the region 64. However, the effective attenuation of the image voxel due to the Compton scatter and photo-electric absorption along this region is unknown, thereby resulting in images with noisy decomposition.

Figure 5:
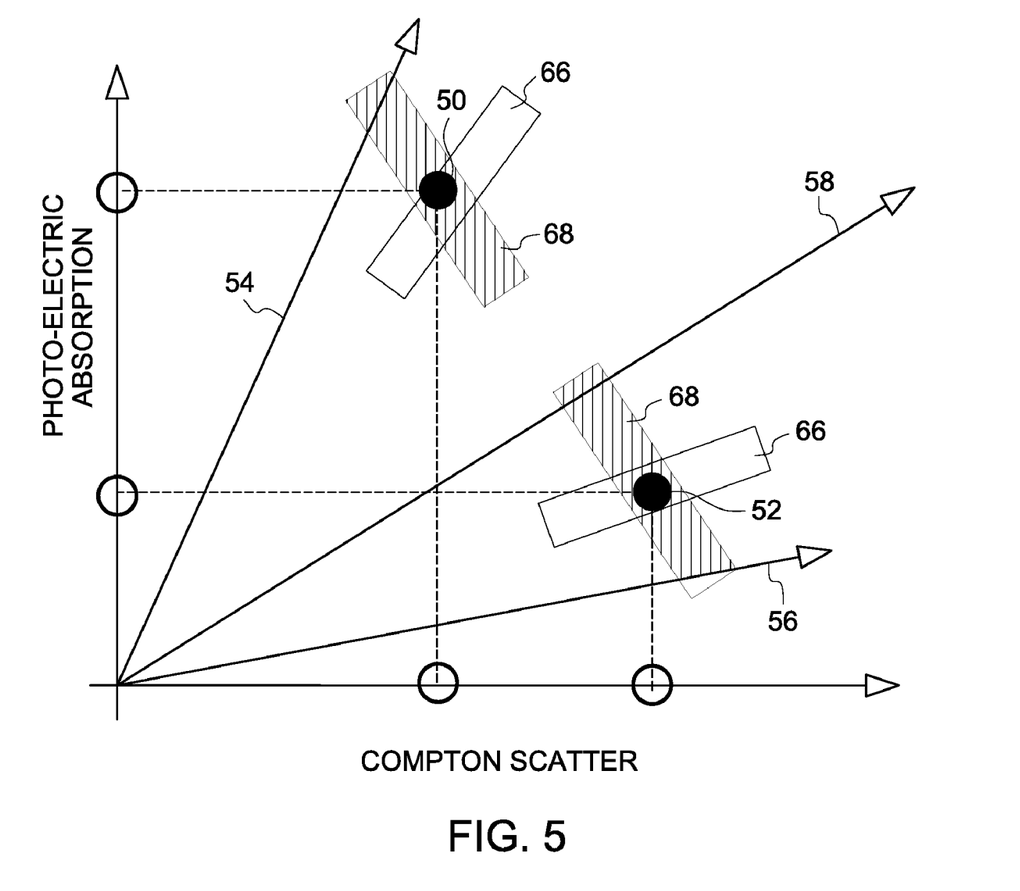
FIG. 5 is a graph illustrating composition and density information in a two-dimensional (2D) space for an image voxel of an imaged object in accordance with yet another embodiment of the present invention.

FIG. 5 is a graph illustrating composition and density information in a two-dimensional (2D) space for an image voxel of an imaged object in accordance with yet another embodiment of the present invention. In a particular embodiment, FIG. 5 is an illustration of prior information in terms of the relationship between the different basis components. Reference numerals 50 and 52 correspond to two image voxels of an imaged object in a 2D space comprising different material compositions, such as for example, bone 54 and water 56. Reference numeral 58 represents the effective attenuation axis. Region 68 corresponds to the effective attenuation of an image voxel. Region 66 corresponds to the prior information associated with an image voxel. As will be described in greater detail below, the prior information along with the information on the effective attenuation of an image voxel may be used to generate a multi-spectral image of an object with improved image quality and reduced noise.

In accordance with embodiments of the present invention, the weight of basis component j for an image voxel i is represented by $(x_{i,j})$. Accordingly, the prior information associated with each image voxel $x_{i,j}$ may be generalized to express dependencies across the components j. In particular, $(x_{i,1})$ may represent the weight/density of an image voxel with respect to one material (such as, for example, water or tissue) and $(x_{i,2})$ may represent the weight/density of an image voxel with respect to another material (such as, for example, bone). Other characterizations may include, for example, a Compton component, $(x_{i,1})$ and a photoelectric component, $(x_{i,2})$. Referring to equation (2) again, for a specific voxel i, equation (2) may be represented as, $\mu_i = x_{i,1} \cdot \Phi(E) + x_{i,2} \cdot \Theta(E)$. More particularly, if $(x_{i,1})$, represents the Compton component of a material and $(x_{i,2})$ represents the photoelectric component, then different material compositions may be represented by different regions in a two-dimensional (2D) space of an imaged object defined by $(x_{i,1})$ and $(x_{i,2})$.

As will be appreciated by those skilled in the art, the prior information in an image voxel, $x_{i,j}$, may be focused on the distribution of $x_{i,j}$ either in terms of the actual range of values taken on by voxels, generally referred to as gamma priors or the relationship between different, spatially proximal voxels, generally referred to as Markov Random Field (MRF) priors. Gamma priors may include, for example, information about possible combinations of $xi_{,1}$ for which $xi_{,1}$ may be really high and $xi,2$ may be very low, or vice versa. MRF priors may be typically expressed as a function, $x_{i,j} - x_{1,j}$, implying that nearby image voxel values are expected to be similar. In a particular embodiment, an MRF prior may be expressed as a quadratic prior as shown in equation (5) below:

$$\phi(x) = \sum_j \sum_i \sum_{l \in N(i)} (x_{ij} - x_{lj})^2 \quad (5)$$

where N(i) is the set of voxels that constitute the neighborhood of voxel i and $\phi(x)$ is the cost function. In particular, the prior expression shown in equation (5) may be generalized to express dependencies across the spectral dimension j.

The cost function $\phi(x)$ represented by equation (5) may be further generalized as shown in equation (6) below:

$$\phi(x) = \sum_j \sum_i \sum_{l \in N(i)} \psi(x_{ij} - x_{lj}) \quad (6)$$

where ψ is an edge preserving regularization function, or in statistical terms, the Probability Density Function (PDF) for the differences between image voxels. As will be appreciated by those skilled in the art, a "Probability Density Function" refers to a function that represents a probability distribution for a given variable or quantity.

In one embodiment, the prior information may be defined to penalize points that do not correspond to known materials in the object. A quadratic (or other) penalty can then be used to penalize deviations from these known material composition-densities. A simple sum of quadratic penalties may be written as shown in equations (7) and (8) below:

$$\phi(x) = \sum_i \min_{l \in L} [(x_{i,1} - a_{l,1})^2 + (x_{i,2} - a_{l,2})^2] \quad (7)$$

$$\phi(x) = \sum_i \prod_{l \in L} [(x_{i,1} - a_{l,1})^2 + (x_{i,2} - a_{l,2})^2] \quad (8)$$

where $a_{1,1}$ and $a_{1,2}$ represent the nominal component decompositions of the $1^{th}$ material in the imaged object. In particular, if a target image voxel consists primarily of bone, soft tissue, contrast and calcium, the basis components comprising these materials may be chosen as "anchors", $a_{1,j}$ and then set up as prior information to penalize large deviations from these values.

The use of prior information in accordance with embodiments of the present invention, results in better material discrimination than an un-regularized solution, with smaller deviations (i.e. less noise) around each anchor point. As used herein, an un-regularized solution refers to a solution that is formed without using prior information. Equation (7) may be further generalized by replacing the quadratic penalty with other penalty functions. In another embodiment, equation (7) may be generalized by rotating and scaling the isocontours of the penalty functions so as to represent the correlations between the basis components in a well-defined manner. In this case, an additional cross term is needed along with scaling coefficients as shown in equation (9) below:

$$\phi(x) = \quad (9)$$

$$\sum_i \min_{l \in L} [c_1(x_{i,1} - a_{l,1})^2 + c_2(x_{i,2} - a_{l,2})^2 + c_3(x_{i,1} - a_{l,1})(x_{i,2} - a_{l,2})]$$

One generalization of equation (9) is based on combining it with a spatial penalty that enables neighboring image voxels to take on the same values. An example of which is, a prior term of the form:

$$\phi(x) = \sum_i \min_{l \in L} c_1(x_{i,1} - a_{l,1})^2 + c_2(x_{i,2} - a_{l,2})^2 + \quad (10)$$

$$c_3(x_{i,1} - a_{l,1})(x_{i,2} - a_{l,2}) + \sum_j \sum_i i \sum_{l \in N(i)} (x_{i,j} - x_{l,j})^2$$

This generalization of the prior term represented by equation (10) results in images that have lower noise and that have well defined material properties.

In accordance with embodiments of the present invention, the prior information associated with each image voxel is defined by a joint probability density (PDF) function between a plurality of basis components comprised in the materials of the imaged object. In a particular embodiment, the PDF is defined as a distribution of the basis components in terms of an absolute voxel range associated with the image voxel. As mentioned above, the basis components may include a Compton component and a photo-electric component.

In another embodiment, the prior information associated with each image voxel $x_i$, is defined by a joint probability density function (PDF) of the ratio between two basis components as shown in equation (11) below:

$$r_i = x_{i,1}/x_{i,2} \quad (11)$$

where, $r_i$ represents the ratio for a given voxel i of the weights corresponding to the two basis components.

Accordingly, the prior term may be expressed by equations (12) or (13) as shown below:

$$\phi(x) = \sum_i \min_{l \in L} \psi(r_i - r_l) \quad (12)$$

$$\phi(x) = \sum_i \prod_{l \in L} \psi(r_i - r_l) \quad (13)$$

In this case, the prior information provides information complementary to the density information. In other words, the density provides information on the average attenuation of the voxel, while the prior term provides information on the ratio between the different constituents that comprise an imaged object.

In an alternate embodiment, the prior information associated with each image voxel is defined by a joint probability density function (PDF) of the differences between neighboring voxel values. For example, some combination of differences between two image voxels, $x_1$ and $x_2$ are more likely than others, because physically differences occur due to changes in density in the same material or changes in material composition. A prior term of this type may be represented by equations (14) or (15) as shown below:

$$\phi(x) = \sum_i \min_{l \in L} [c_{1,l}\delta_{i,j,1}^2 + c_{2,l}\delta_{i,j,2}^2 + c_{3,l}\delta_{i,j,1}\delta_{i,j,2}] \quad (14)$$

$$\phi(x) = \sum_i \prod_{l \in L} [c_{1,l}\delta_{i,j,1}^2 + c_{2,l}\delta_{i,j,2}^2 + c_{3,l}\delta_{i,j,1}\delta_{i,j,2}] \quad (15)$$

where, $\delta_{i,j,1} = x_{i,1} - x_{j,1}$ and represents the difference in the weights for component 1 for voxel i versus voxel j and $c_i$ represents the coefficients that define the shape and size of the penalty function $\phi$ that defines the prior information.

As will be appreciated by those skilled in the art, equations (14) and (15) represent super positions of rotated elliptical probability density functions in the differences between nearby voxels.

In another aspect of the present invention, the prior information may be incorporated into the cost function of an iterative reconstruction algorithm to achieve the desired properties of the image, including noise reduction (through increased selective smoothing of the image) and better material decompositions (through the incorporation of known nominal material properties into the spectral coefficients for each voxel). In one embodiment, the iterative reconstruction algorithm may be selected from the group consisting of maximum likelihood (ML) techniques and maximum a posteriori (MAP) techniques.

As will be appreciated by those skilled in the art, iterative reconstruction techniques, in general, start with an image estimate. This image estimate is updated and transformed back and forth between the projection domain and the image domain. The particular manner in which transformation between the domains is performed distinguishes different reconstruction techniques. For instance, Iterative Filtered Backprojection (IFBP) methods use FBP to transform to an image and they use a Radon transform or forward projection to calculate a sinogram.

More specifically, in an iterative reconstruction technique, a calculated sinogram (i.e., a set of predicted projection data) is compared with the actual measured sinogram data. The calculated sinogram is a transformation from an estimated reconstructed image. In the first iteration, the reconstructed image may be any appropriate default setting. As a result of the comparison of the calculated sinogram and the measured sinogram, a sinogram error is produced. The sinogram error is then transformed back to the image domain to produce a correction image. Thus, in a subsequent iteration, the correction image is used along with the previous reconstructed image to create an updated reconstructed image for the next iteration. Thereafter, the process is repeated for a desired number of iterations or until some optimization stopping criterion is met.

As will be appreciated by those skilled in the art, a forward measurement model between unknown distributions representing an imaged object and projection data may generally be represented by equation (16) as shown below:

$$I_k(m) = \int_E S_k(E) e^{-\sum_j \sum_i a_{m,i} x_{i,j} \mu_j(E)} dE \quad (16)$$

where k denotes an index to the measurement spectrum (each k represents an energy spectrum or a kVp), m is a sinogram index, $a_{m,i}$ is the contribution of an image voxel i to a sinogram element m and defines the system model that captures the geometry of the system, $\mu_j(E)$ represents the energy-dependence of the attenuation of component j, $S_k(E)$ represents the probability distribution for detection of photons at energy E, in the absence of an object (air scan).

As will be appreciated by those skilled in the art, an iterative reconstruction algorithm typically determines voxel values, $x_{i,j}$ given noisy measurements of $I_k(m)$ by forming a sequence of images that minimize a cost function. The choice of the cost function to be minimized and the generation of the sequence of images form the two primary components of an iterative reconstruction algorithm. The nature of the cost function may depend on the statistical model for the errors in the measurements. If the errors are normally distributed, then a weighted least squares (WLS) cost function is obtained as shown in equation (17) below:

$$J(x) = \sum_k \sum_m (I_k(m) - \tilde{I}_k(m))^2 \tilde{w}_{k,m} \quad (17)$$

where, $w_{k,m}$ is the weight function that characterizes the accuracy of the sinogram measurement $I_k(m)$ and $\tilde{I}$ represents the measured intensities. The images formed from minimization of equation (17) are typically noisy. In addition, the imaging equation (17) may not provide enough information to properly resolve the various components of an image voxel. In both situations, the prior information on the image voxel can be used to improve the quality of the solution. In practice, by using a cost function that contains a data fit term as shown in equation (17) and a prior term as shown in equations (5)-(15), the total cost=$J(x)+\phi(x)$.

The use of prior information in accordance with embodiments of the present technique may be applied independent of the type of cost function used or the optimization method employed in the iterative reconstruction. For example, cost functions based on a normal distribution may be used leading to weighted least squares cost functions. Alternately, a Poisson noise model may be used for the errors in measurement that (in the absence of a prior) lead to maximum likelihood formulations of the problem. The optimization method may also vary to include simultaneous update solutions, such as Conjugate Gradients or Maximum Likelihood Transmission Reconstruction or use iterative co-ordinate descent methods.

Figure 6:
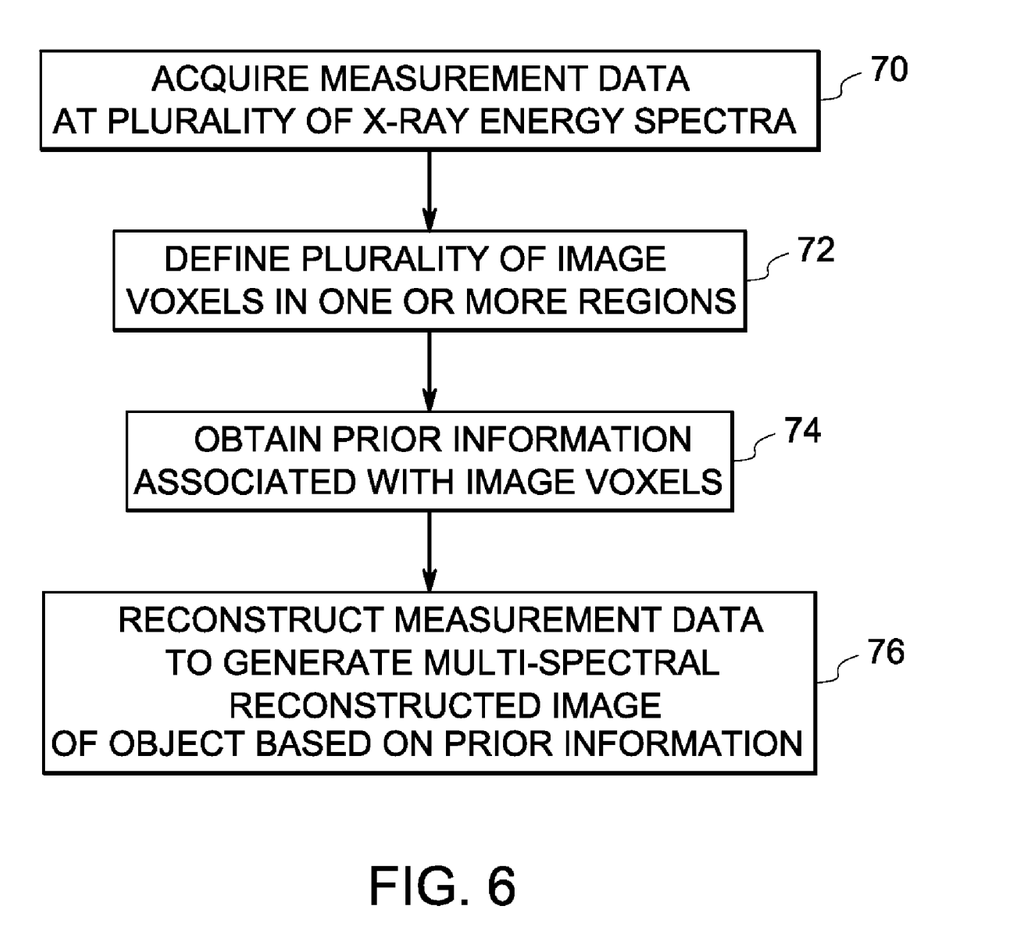
FIG. 6 illustrates a process for generating a multi-spectral image of an object in accordance with one embodiment of the present invention.

FIG. 6 illustrates a process for generating a multi-spectral image of an object in accordance with one embodiment of the present invention. In step 70, measurement data is acquired at a plurality of X-ray energy spectra. In one embodiment, the measurement data comprises at least one of density line integral measurements, photo-electric line integral measurements and Compton line integral measurements.

In step 72, a plurality of image voxels are defined in one or more regions comprising the object. In step 74, prior information associated with the plurality of image voxels is obtained. In one embodiment, and as mentioned above, the prior information is defined by a joint probability density function (PDF) between a plurality of basis components. In one embodiment, the plurality of basis components comprise one or more material compositions distributed in different regions in a two-dimensional (2D) space. The one or more material compositions comprise at least one of tissue, water or bone. In another embodiment, the plurality of basis components comprise a Compton component and a Photoelectric component.

In one embodiment, the joint probability density function (PDF) is defined as a distribution of the basis components in terms of an absolute voxel value range associated with the plurality of image voxels. In another embodiment, the prior information is defined by a joint probability density function (PDF) of the differences between neighboring image voxel values. In yet another embodiment, the prior information is defined by a joint probability density function (PDF) of the ratio between the one or more basis components.

In step 76, the measurement data is reconstructed to generate a multi-spectral reconstructed image of the object based on the prior information. In one embodiment, an iterative reconstruction technique is used to generate the multi-spectral reconstructed image of the object.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for generating a multi-spectral image of an object, the method comprising:
acquiring x-ray transmission measurement data at a plurality of X-ray energy levels;
defining a plurality of image voxels in one or more regions comprising the object, each of the plurality of image voxels having a linear attenuation associated therewith;
obtaining prior information associated with the plurality of image voxels, wherein the prior information is defined by a joint probability density function (PDF) between a plurality of basis components, and wherein a combination of the plurality of basis components represents the linear attenuation of the plurality of image voxels; and
reconstructing the x-ray transmission measurement data using the prior information to generate a multi-spectral reconstructed image of the object based on the prior information.

2. The method of claim 1, wherein the prior information comprises composition and density information of one or more material compositions in the attenuation co-efficients of the object.

3. The method of claim 1, wherein the measurement data comprises at least one of density line integral measurements, photo-electric line integral measurements and Compton line integral measurements.

4. The method of claim 1, wherein the plurality of basis components comprise one or more material compositions distributed in different regions in a two-dimensional (2D) space comprising the object.

5. The method of claim 4, wherein one or more material compositions comprise at least one of tissue, water or bone.

6. The method of claim 4, wherein the plurality of basis components comprise at least one of a Compton component and a Photoelectric component.

7. The method of claim 1, wherein the joint probability density function (PDF) is defined as a distribution of the basis components in terms of an absolute voxel value range associated with the plurality of image voxels.

8. The method of claim 1, wherein the prior information is defined by a joint probability density function (PDF) of the differences between neighboring image voxel values.

9. The method of claim 1, wherein the prior information is defined by a joint probability density function (PDF) of the ratio between the plurality of basis components.

10. The method of claim 1, further comprising using an iterative reconstruction technique to generate the multi-spectral reconstructed image of the object.

11. The method of claim 10, wherein the iterative reconstruction algorithm is selected from the group consisting of maximum likelihood (ML) techniques and maximum a posteriori (MAP) techniques.

12. An image analysis system, comprising:
an X-ray source configured to emit a stream of radiation;
a detector configured to detect the stream of radiation to generate one or more signals responsive to the stream of radiation, wherein the detector comprises a plurality of detector elements;
a system controller configured to control the X-ray source and to acquire x-ray transmission measurement data at a plurality of X-ray energy levels from one or more of the detector elements via a data acquisition system; and
a computer configured to:
define a plurality of image voxels in one or more regions comprising the object;
define a linear attenuation associated with each of the plurality of image voxels as a combination of a plurality of basis functions, each of the plurality of basis functions having a respective basis coefficient associated therewith;
obtain prior information associated with the plurality of image voxels comprising the object, wherein the prior information is defined by a joint probability density function (PDF) between the plurality of basis coefficients; and reconstruct the x-ray transmission measurement data to generate a multi-spectral reconstructed image of the object based on the prior information.

13. The image analysis system of claim 12, wherein the prior information comprises composition and density information of one or more material compositions in the attenuation co-efficients of the object.

14. The image analysis system of claim 12, wherein the measurement data comprises at least one of density line integral measurements, photo-electric line integral measurements and Compton line integral measurements.

15. The image analysis system of claim 12, wherein the plurality of basis components comprise one or more material compositions distributed in different regions in a two-dimensional (2D) space comprising the object.

16. The image analysis system of claim 15, wherein one or more material compositions comprise at least one of tissue, water and bone.

17. The image analysis system of claim 15, wherein the plurality of basis functions represent at least one of a Compton component and a Photoelectric component.

18. The image analysis system of claim 12, wherein the joint probability density function (PDF) is defined as a distribution of basis components in terms of an absolute voxel value range associated with the plurality of image voxels.

19. The image analysis system of claim 12, wherein the prior information is defined by a joint probability density function (PDF) of the differences between neighboring image voxel values.

20. The image analysis system of claim 12, wherein the prior information is defined by a joint probability density function (PDF) of the ratio between one or more basis components.

21. The image analysis system of claim 12, further comprising using an iterative reconstruction technique to generate the multi-spectral reconstructed image of the object, and wherein the iterative reconstruction algorithm is selected from the group consisting of maximum likelihood (ML) techniques and maximum a posteriori (MAP) techniques.

\* \* \* \* \*